United States Patent
Partington et al.

(10) Patent No.: US 10,144,679 B2
(45) Date of Patent: *Dec. 4, 2018

(54) PROCESS FOR PREPARING ETHENE

(71) Applicant: Technip E&C Limited, Milton Keynes (GB)

(72) Inventors: Stephen Roy Partington, East Yorkshire (GB); Stephen James Smith, East Yorkshire (GB); Nakul Thakar, East Yorkshire (GB)

(73) Assignee: Technip E&C Limited, Milton Keynes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/529,136

(22) PCT Filed: Nov. 19, 2015

(86) PCT No.: PCT/EP2015/077133
§ 371 (c)(1),
(2) Date: May 24, 2017

(87) PCT Pub. No.: WO2016/083241
PCT Pub. Date: Jun. 2, 2016

(65) Prior Publication Data
US 2017/0260113 A1     Sep. 14, 2017

(30) Foreign Application Priority Data
Nov. 24, 2014 (EP) .................... 14194604

(51) Int. Cl.
| | | |
|---|---|---|
| *C07C 1/24* | (2006.01) | |
| *B01J 23/30* | (2006.01) | |
| *B01J 37/08* | (2006.01) | |
| *B01J 23/00* | (2006.01) | |
| *B01J 27/188* | (2006.01) | |

*B01J 35/02* (2006.01)
(Continued)

(52) U.S. Cl.
CPC ............. *C07C 1/24* (2013.01); *B01J 23/002* (2013.01); *B01J 23/30* (2013.01); *B01J 27/188* (2013.01);
(Continued)

(58) Field of Classification Search
None
See application file for complete search history.

(56) References Cited

U.S. PATENT DOCUMENTS 9,199,845 B2 * 12/2015 Gracey ............... B01J 23/30
2010/0056838 A1 * 3/2010 Potter .................. C07C 1/24
                                                               585/639

(Continued)

FOREIGN PATENT DOCUMENTS

| EP | 1792885 | 6/2007 |
|----|---------|--------|
| EP | 1925363 | 5/2008 |

(Continued)

OTHER PUBLICATIONS

Chang et al., "A Lumped Kinetic Model for Dehydration of Ethanol to Hydrocarbons Over HZSM-5," Chem. Eng Comm. 1990, 95, pp. 27-39.

(Continued)

*Primary Examiner* — Philip Y Louie
(74) *Attorney, Agent, or Firm* — Porzio, Bromberg & Newman P.C.

(57) ABSTRACT

The present invention provides a process for the preparation of ethene by vapor phase chemical dehydration of a feed-stream comprising ethanol and optionally water and/or ethoxy ethane, said process comprising contacting a dried supported heteropolyacid catalyst in a reactor with the feed-stream having a feed temperature of at least 200° C.; wherein before the supported heteropolyacid catalyst is contacted with the feed-stream having a feed temperature of (Continued)

Figure 1:
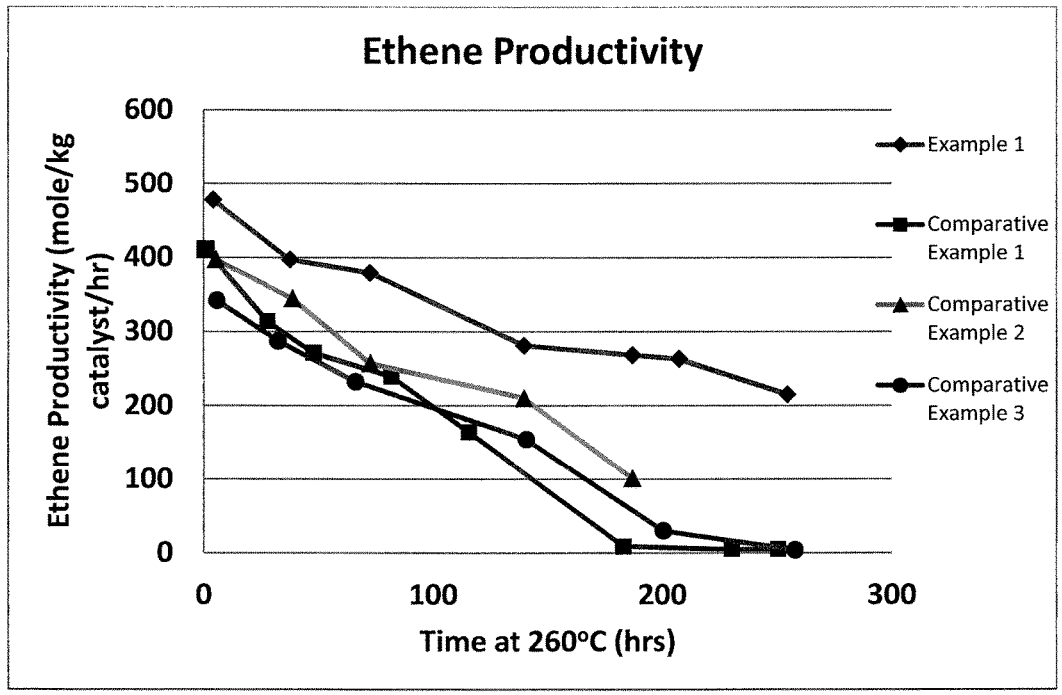

at least 200° C., the process is initiated by: (i) drying a supported heteropolyacid catalyst in a reactor under a stream of inert gas having a feed temperature of from above 100° C. to 200° C.; and (ii) contacting the dried supported heteropolyacid catalyst with an ethanol-containing vapor stream having a feed temperature of from above 100° C. to 160° C.

20 Claims, 1 Drawing Sheet

(51) Int. Cl.
  *B01J 35/10* (2006.01)
  *B01J 37/02* (2006.01)
  *B01J 21/08* (2006.01)

(52) U.S. Cl.
  CPC ......... *B01J 35/023* (2013.01); *B01J 35/1019* (2013.01); *B01J 35/1042* (2013.01); *B01J 35/1061* (2013.01); *B01J 37/0201* (2013.01); *B01J 37/08* (2013.01); *B01J 21/08* (2013.01); *B01J 35/1076* (2013.01); *B01J 2523/00* (2013.01); *C07C 2521/08* (2013.01); *C07C 2523/30* (2013.01); *Y02P 20/52* (2015.11)

(56) References Cited

U.S. PATENT DOCUMENTS

| | | | | |
|---|---|---|---|---|
| 2010/0249481 | A1* | 9/2010 | Gracey | C07C 1/20 585/639 |
| 2012/0165589 | A1* | 6/2012 | Partington | C07C 1/24 585/639 |
| 2012/0302810 | A1* | 11/2012 | Partington | B01J 27/188 585/639 |
| 2012/0310026 | A1* | 12/2012 | Partington | C07C 1/20 585/639 |
| 2017/0121238 | A1* | 5/2017 | Partington | C07C 1/24 |
| 2017/0349504 | A1 | 12/2017 | Partington et al. | |
| 2017/0354959 | A1* | 12/2017 | Partington | B01J 27/188 |
| 2018/0009725 | A1* | 1/2018 | Partington | C07C 1/24 |

FOREIGN PATENT DOCUMENTS

| | | |
|---|---|---|
| WO | WO-2007/003899 | 1/2007 |
| WO | WO-2007/063281 | 6/2007 |
| WO | WO-2011/104495 | 9/2011 |

OTHER PUBLICATIONS

Yue et al., "Kinetic Analysis of the Catalytic Dehydration of Alcohols over Zeolites," Chem. Eng. Res and Design 1984; 62: pp. 81-91.

Barrett et al., "The Determination of Pore Volume and Area Distributions in Porous Substances. I. Computations from Nitrogen Isotherms," J. Am Chem. Soc., 1951, 73(1), pp. 373-380.

Brunauer et al., "Adsorption of Gases in Multimolecular Layers," J. Amer. Chem. Soc. 1938, 60(2), pp. 309-319.

International Search Report and Written Opinion for PCT/EP2015/077133 dated Jan. 25, 2016.

* cited by examiner

PROCESS FOR PREPARING ETHENE

The present invention relates to a process for producing ethene by the vapour phase dehydration of ethanol using a heteropolyacid catalyst. In particular, the process of the present invention involves an initiation procedure comprising drying of the heteropolyacid catalyst at a specific range of temperature prior to use in an ethanol dehydration reaction.

Ethene is an important commodity chemical and monomer which has traditionally been produced industrially by the steam or catalytic cracking of hydrocarbons derived from crude oil. However there remains an increasing need to find alternative economically viable methods of making this product. By virtue of its ready availability from the fermentation of biomass and synthesis gas based technologies, ethanol is emerging as an important potential feedstock from which ethene can be made in the future.

The production of ethene by the vapour phase chemical dehydration of ethanol is a well-known chemical reaction which has been operated industrially for many years (see for example Kirk Othmer Encyclopaedia of Chemical Technology (third edition), Volume 9, pages 411 to 413). Traditionally this reaction has been carried out in the presence of an acid catalyst such as activated alumina or supported phosphoric acid.

In recent years attention has turned to finding alternative catalysts having improved performance. This has led to the use of supported heteropolyacid catalysts, such as those disclosed in EP1925363, which have the benefit of improved selectivity, productivity and reduced ethane formation following the dehydration of a feedstock comprising ethanol and ethoxyethane for the production of ethene. This is desirable because firstly ethane is an undesirable by-product and secondly its separation from ethene on a large scale is both difficult and energy intensive. Related documents WO 2007/063281 and WO 2007/003899 also disclose modes of carrying out dehydration of oxygenate feedstocks with supported heteropolyacid catalysts. Supported heteropolyacid catalysts may be readily prepared using wet impregnation techniques by dissolving a heteropolyacid in a suitable solvent to form a heteropolyacid solution and then impregnating a suitable catalyst support with the heteropolyacid solution.

In the dehydration process, a feed typically comprising ethanol, and optionally water and other components, is continuously fed to a reactor containing a bed of heteropolyacid catalyst and the products continuously removed. Under steady state conditions, the feed entering the reactor is rapidly converted near the inlet into an equilibrium mixture of water, ethanol and ethoxyethane (the product of a rapid first stage dehydration of the ethanol). Such processes are typically conducted at elevated temperature and pressure.

Due to i) the nature of heteropolyacids; ii) the process for preparing supported heteropolyacid catalysts; and iii) the loading of said catalysts into a reaction zone, the heteropolyacid component will almost certainly be exposed to water (such as moisture in the atmosphere) under conditions at which it may become bound to the heteropolyacid component. Thus the hydration state of the heteropolyacid component of the supported heteropolyacid catalyst prior to heating the supported heteropolyacid catalyst will be above zero (i.e. the heteropolyacid component of the supported heteropolyacid catalyst has water molecules chemically bound thereto). Typically, the hydration state of a heteropolyacid decreases on exposure to increasing temperature; that is, the number of water molecules bound to the heteropolyacid decreases with increasing temperature. The degree of hydration of the heteropolytungstic acid may affect the acidity of the supported catalyst and hence its activity and selectivity.

WO 2011/104495 discloses a dehydration process for the preparation of alkene using a supported heteropolyacid catalyst. That document teaches an initial catalyst drying step conducted at a temperature of at least 220° C., so as to remove bound water such that at least part of the heteropolyacid component of the catalyst has a hydration state of zero, followed by a reduction in temperature under anhydrous atmosphere, before the catalyst is contacted with the reactant feedstream. WO 2011/104495 teaches that the drying step advantageously leads to improved ethane selectivity of the catalyst in the subsequent ethanol dehydration reaction.

It has thus now become desirable to dry the supported heteropolyacid catalyst at high temperatures, typically around 240° C., as part of the start-up procedure preceding ethanol dehydration. However, one problem that has hitherto not been acknowledged relates to catalyst deactivation. It has been found that when the supported heteropolyacid catalyst is dried at such high temperatures, deactivation of the heteropolyacid catalyst is exacerbated. Without being bound by any particular theory, this is believed to occur as a result of undesirable side reactions with high activation energies, which contribute to deactivation, becoming more prevalent as a result of the higher temperatures being used.

In particular, the number of heteropolyacid decomposition sites formed on the surface of the catalyst support is believed to increase during the high-temperature drying step, or such decomposition sites are 'seeded' during the drying step and subsequently develop into decomposition sites during the dehydration reaction. Mobility of heteropolyacid at the surface of the support toward such 'seed' sites is also believed to compound the problem.

Replacement of the catalyst in a dehydration system is labour intensive, has significant materials costs and involves temporarily shutting down what is likely to be a continuous process, which has detrimental impact on product output. Thus, a problem of catalyst deactivation poses a serious issue to the economic viability of ethanol dehydration processes.

It has now surprisingly been found that catalyst lifetime in an ethanol dehydration reaction can be extended by performing a drying step, before committing the supported heteropolyacid catalyst to the ethanol dehydration reaction, at lower temperatures than taught in the prior art. By performing the drying step over a specific range of intermediate temperatures immediately followed by contacting with an ethanol-containing vapour stream over another specific range of temperatures as part of the start-up procedure for ethanol dehydration, productivity loss over time as a result of catalyst deactivation is significantly reduced. Furthermore, at least in some embodiments, the maximum ethene productivity (mole/kg catalyst/hr) may also be increased.

According to the present invention, there is provided a process for the preparation of ethene by vapour phase chemical dehydration of a feed-stream comprising ethanol and optionally water and/or ethoxyethane, said process comprising contacting a dried supported heteropolyacid catalyst in a reactor with the feed-stream having a feed temperature of at least 200° C.; and wherein before the supported heteropolyacid catalyst is contacted with the feed-stream having a feed temperature of at least 200° C., the process is initiated by:

(i) drying a supported heteropolyacid catalyst in a reactor under a stream of inert gas having a feed temperature of from above 100° C. to 200° C.; and (ii) contacting the dried and supported heteropolyacid catalyst with an ethanol-containing vapour stream having a feed temperature of from above 100° C. to 160° C.

Preferably, the initiation of the ethanol dehydration process further comprises: (iii) ramping the feed temperature of the ethanol-containing vapour stream to at least 200° C., preferably over the course of 10 minutes to 8 hours, more preferably over the course of 20 minutes to 4 hours.

It has been surprisingly found that an ethanol dehydration process is particularly advantageous when initiated by drying the supported heteropolyacid catalyst and contacting with an ethanol-containing vapour stream at the above temperature ranges. In particular, this initiation procedure reduces the level of heteropolyacid catalyst deactivation observed in the ethanol dehydration reaction and, at least in some embodiments, increases ethene maximum productivity.

Moreover, it has been found that productivity in a process for producing ethene by the vapour phase dehydration of ethanol using a heteropolyacid catalyst is improved by operating at high temperature; in particular at temperatures higher than those exemplified in the prior art, for example higher than 240° C. However, it has been found that higher operating temperatures also exacerbate catalyst deactivation, much like the high temperature drying steps used in start-up procedures in the prior art. Nevertheless, it has also been surprisingly found that by drying the supported heteropolyacid catalyst and contacting with an ethanol-containing vapour stream at the temperatures recited hereinbefore, catalyst deactivation associated with subsequently operating the ethanol dehydration reaction at higher than conventional temperatures is reduced. Thus, the drying and contacting steps (i) and (ii) which precede the ethanol dehydration reaction in accordance with the process of the present invention, allows the full benefit of higher ethene productivity to be realised whilst avoiding significant catalyst deactivation.

Mechanisms by which the supported heteropolyacids are believed to undergo deactivation during operation include: i) neutralisation by inorganic cations, such as ammonia/ammonium cations, and organic nitrogen-containing compounds; ii) carbon deposition; and iii) decomposition of the heteropolyacid to its constituent oxides. Deactivation as a result of neutralisation by inorganic cations and organic nitrogen-containing compounds may be mitigated by committing the ethanol based raw materials to a clean-up procedure to remove the neutralising species. In contrast, the features of the initiation procedure according to the present invention are believed to largely eliminate deactivation of the heteropolyacid catalyst as a result of decomposition of the heteropolyacid to its constituent oxides.

During the preparation of a supported heteropolyacid catalyst, the catalyst may be optionally dried. However, as the skilled person will appreciate, the supported catalyst will inevitably be exposed to moisture upon transport and introduction into a reactor. Drying removes condensed water vapour from the surface of the support which can negatively impact the surface chemistry of the support, for instance, the acidity of the heteropolyacid component. However, drying inside the reactor in accordance with the present invention has also been surprisingly found to reduce the formation of heteropolyacid decomposition sites on the catalyst.

Without being bound by any particular theory, it is believed that the low temperature drying according to step (i) of the process reduces the possibility of forming 'seed' sites which may subsequently lead to decomposition. 'Seed' sites may be produced following, for example, changes in the oxidation state of the heteropolyacid on exposure to heat; the formation of carbon residues; and/or formation of defect structures. Where exposure to heat has given rise to chemical changes in the heteropolyacid at a specific surface location to form such 'seed' sites, the likelihood of full decomposition of heteropolyacid to its constituent oxides at these sites is substantially increased. Moreover, mobility of heteropolyacid at the surface of the support at elevated temperatures towards such 'seed' sites exacerbates the rate of decomposition. As a consequence, the catalyst lifetime is significantly extended, which has clear economic benefits relating to re-use and replacement of the catalyst, as well as the reduction of waste. The operating conditions of the present invention thus correspond to a narrow window within which significant catalyst deactivation is avoided, whilst ethylene productivity is promoted.

In accordance with the present invention, the supported heteropolyacid catalyst is dried in step (i) of the initiation under a stream of inert gas having a feed temperature of from above 100° C. to 200° C. Preferably, the supported heteropolyacid catalyst is dried in step (i) under a stream of inert gas having a feed temperature of from 100° C. to 180° C.; more preferably from 110° C. to 170° C.; most preferably from 120° C. to 160° C.; for example 150° C.

Reference herein to "initiated" or "initiation" in regard to steps (i) and (ii) of the process of the present invention is intended to mean that these steps precede exposure of the catalyst to the feed-stream at a feed temperature of at least 200° C. Furthermore, "initiated" or "initiation" is also intended to mean that no other steps materially affecting the composition or nature of the supported heteropolyacid catalyst are undertaken before step (i), after the supported heteropolyacid catalyst is positioned within the reactor.

Reference herein to "inert gas" is intended to mean a gas that is not consumed in the reaction of the process of the present invention, and is not consumed by any other process which may be catalysed by the supported heteropolyacid catalyst. Examples of suitable inert gases are nitrogen, argon, helium, methane and carbon dioxide. Preferably, the inert gas is selected from nitrogen, argon and helium, more preferably, the inert gas is nitrogen. By the term "stream of inert gas" as used herein, it is meant that the atmosphere under which the drying step takes place is an inert gas that is constantly being removed and replenished with fresh (or recycled) inert gas (i.e. a gas flow). For example, the "stream of inert gas" is preferably a stream of nitrogen gas.

Reference herein to "drying" is intended to mean exposing the supported heteropolyacid catalyst to heat such that the dew point of water vapour in the reactor, and any other vapour that may be present, is exceeded under the pressure at which the reactor is operated. The low temperature drying of the supported heteropolyacid as part of an initiation procedure for an ethanol dehydration reaction in accordance with the process of the present invention has been found to have numerous benefits with regard to the dominant surface chemistry of the supported heteropolyacid catalyst.

Drying of the supported heteropolyacid catalyst in accordance with the process of the invention is undertaken for a period of at least one hour. Preferably, drying is undertaken for a period of from 1 to 48 hours, more preferably from 2 to 16 hours, most preferably 2 to 12 hours. In some embodiments, the drying time includes a period of time in which the feed temperature of the inert gas for drying is ramped up to match a higher feed temperature used for the subsequent step of contacting with an ethanol-containing vapour stream. Whilst not wishing to be bound by any theory, it is thought that minimizing the period of constant temperature, following a ramped increase of the feed temperature of the inert gas temperature and prior to contact with the ethanol-containing vapour stream, is commercially advantageous.

In accordance with the present invention, the dried supported heteropolyacid catalyst is contacted in step (ii) of the initiation with an ethanol-containing vapour stream having a feed temperature of from above 100° C. to 160° C. Preferably, the dried supported heteropolyacid catalyst is contacted in step (ii) with an ethanol-containing vapour stream having a feed temperature of from 120° C. to 158° C., more preferably from 130° C. to 156° C., even more preferably from 140° C. to 154° C., most preferably from 148° C. to 152° C., for example 150° C.

Reference herein to an "ethanol-containing vapour stream" is intended to mean a gaseous stream comprising at least 50 wt. % ethanol and the balance being made up of diluents. Preferably, the ethanol-containing vapour stream comprises 80 wt. % or more ethanol, more preferably 90 wt. % or more; most preferably 95 wt. % or more; with the balance preferably being made up of inert gas diluents. Suitable inert gas diluents are nitrogen, argon, helium, methane and carbon dioxide. Preferably, the inert gas diluents are selected from nitrogen, argon and helium, more preferably, the inert gas diluent is nitrogen. The amount of water in the ethanol-containing vapour stream is at most 10 wt. %, preferably at most 7 wt. %, more preferably at most 5 wt. %, even more preferably at most 3 wt. %, and still more preferably at most 2 wt. %, based on the total weight of ethanol-containing vapour stream. The amount of ethoxyethane in the ethanol-containing vapour stream is at most 5 wt. %, preferably at most 3 wt. %, and more preferably at most 2 wt. %, based on the total weight of ethanol-containing vapour stream. Most preferably, the ethanol-containing vapour stream is anhydrous or the ethanol-containing vapour stream comprises or consists essentially of ethanol and any balance is made up of inert gas diluents. As will be appreciated, in some embodiments, the ethanol-containing vapour stream may be identical in composition to the feed-stream containing ethanol which undergoes ethanol dehydration. However, in preferred embodiments, the ethanol-containing vapour stream is different from the feed-stream containing ethanol.

Step (ii) of contacting the dried supported heteropolyacid catalyst with an ethanol-containing vapour stream has been found to be of particular benefit in obtaining steady state conditions for the ethanol dehydration reaction and enhancing catalyst performance. Furthermore, contacting the catalyst with an ethanol-containing vapour stream at a temperature of from above 100° C. to 160° C. ensures that detrimental exotherms are avoided, which can lead to undesirable competing oligomerisation reactions during the subsequent ethanol dehydration of the feed-stream. In a particularly preferred embodiment, the inert gas stream which is used for drying the supported heteropolyacid in step (i) is converted to an ethanol-containing vapour stream for contacting step (ii) by addition of ethanol vapour to the inert gas stream.

The dehydration of the feed-stream according to the present invention is believed (Chem. Eng Comm. 1990, 95, 27 to 39) to proceed by either the direct dehydration to olefin(s) and water (Equation 1); or via an ether intermediate (Equations 2 and 3).

  (1)

  (2)

  (3)

The direct conversion of the ether to two moles of olefin and water has also been reported (Chem. Eng. Res. and Design 1984, 62, 81 to 91). All of the reactions shown above are typically catalysed by Lewis and/or Bronsted acids. Equation 1 shows the endothermic direct elimination of ethanol to ethene and water; competing with Equation 1 are Equations 2 and 3 i.e. the exothermic etherification reaction (Equation 2), and the endothermic elimination of ethoxyethane to produce ethene and ethanol (Equation 3). However, the dehydration reaction of ethanol to ethene is overall said to be endothermic.

The present invention provides a process for the preparation of ethene by vapour phase chemical dehydration of a feed-stream comprising ethanol and optionally water and/or ethoxyethane, said process comprising contacting a dried supported heteropolyacid catalyst in a reactor with the feed-stream having a feed temperature of at least 200° C.; wherein before the dried supported heteropolyacid catalyst is contacted with the feed-stream having a feed temperature of at least 200° C., the process is initiated by: (i) drying a supported heteropolyacid catalyst in a reactor under a stream of inert gas having a feed temperature of from above 100° C. to 200° C.; and (ii) contacting the dried supported heteropolyacid catalyst with an ethanol-containing vapour stream having a feed temperature of from above 100° C. to 160° C.

Preferably, the feed-stream comprises water and/or ethoxyethane, more preferably the feed-stream comprises water and ethoxyethane. When both ethoxyethane and water are present in the feed-stream, it is preferred that the molar ratio of ethoxyethane to water is from 3:1 to 1:3, preferably from 3:1 to 1:1, more preferably 2:1 to 1:1.

Suitably, the amount of water in the feed-stream of the process of the present invention is at most 50 wt. %, more preferably at most 20 wt. %, most preferably at most 10 wt. %, or even at most 7 wt. %, based on the total weight of water, ethanol and ethoxyethane in the feed-stream. Preferably, the amount of water in the feed-stream is at least 0.1 wt. %, more preferably at least 0.5 wt. % and most preferably at least 1 wt. %, based on the total weight of water, ethanol and ethoxyethane in the feed-stream.

Suitably, the amount of ethoxyethane in the feed-stream of the process of the present invention is at most 50 wt. %, more preferably at most 40 wt. %, most preferably at most 35 wt. % based on the total weight of water, ethanol and ethoxyethane in the feed-stream. Preferably, the amount of ethoxyethane in the feed-stream is at least 0.1 wt. %, more preferably at least 0.5 wt. % and most preferably at least 1 wt. %, based on the total weight of water, ethanol and ethoxyethane in the feed-stream.

The liquid product stream following olefin removal comprises mostly unreacted ethanol, ethoxyethane and water. The applicants have found that it is particularly preferable to recycle the major portion of the alcohols and ethers back to the vapour phase dehydration reactor after water removal.

In some embodiments of the invention, the feed-stream comprises an inert gas diluent. In other embodiments, an inert gas diluent is added down the catalyst bed, or between multiple catalyst beds arranged in series or in parallel, if used. Preferred diluents for the feed-stream include nitrogen, helium, ethene and/or saturated hydrocarbons, for example hexanes, 2-methylpropane or n-butane. More preferably, the feed-stream diluent is selected from nitrogen and/or helium.

As described above, it has now been found that higher temperatures used for the dehydration reaction give greater ethene productivity. Since the present invention diminishes the negative effects of high operating temperatures on catalyst deactivation, it is preferred that the dried supported heteropolyacid is contacted with the feed-stream when it has a feed temperature of at least 220° C., more preferably at least 240° C. In particular preferred embodiments, the feed temperature is at least 252° C., at least 255° C., at least 260° C., at least 280° C. or even at least 300° C. The upper limit of the feed temperature of the feed-stream is below the temperature at which selectivity for ethene is negatively impacted and/or one which is overly energy intensive. Preferably, the upper limit of the feed temperature of the feed-stream is 350° C., more preferably 325° C. Reference to "feed temperature" herein is intended to refer to the temperature of a particular stream at the point at which it is fed to the reactor.

The pressure inside the reactor during the dehydration reaction when the supported heteropolyacid catalyst is contacted with the feed-stream is preferably in the range of from 0.1 MPa to 4.5 MPa, more preferably at a pressure in the range of from 0.5 MPa to 3.5 MPa, and most preferably at a pressure in the range of from 1.0 MPa to 2.8 MPa.

Reference herein to the pressure inside the reactor corresponds to the sum of the partial pressures of the reactants, namely those of ethanol, water and ethoxyethane, as well as the partial pressure of the ethene product. Unless otherwise indicated herein, partial pressures of inert gas diluents, such as helium and nitrogen, or other inert components are excluded from the total stated pressure. Thus, reference to reactor pressure herein is in accordance with the formula: $P_{reactor}=P_{water}+P_{ethanol}+P_{ethoxyethane}+P_{ethene}$. Furthermore, unless otherwise indicated, reference to reactor pressures herein is to absolute pressures, and not gauge pressures.

As will be appreciated by the skilled person, there is often a pressure drop that occurs in a dehydration reactor between the point where the feed stream enters the reactor and that where the effluent stream emerges from the reactor. As a consequence, there is, to a varying extent, an internal pressure gradient which exists inside the reactor itself. It is therefore to be understood that reference herein to the "pressure inside the reactor" means any pressure falling within the pressure range defined by the above-mentioned internal pressure gradient. The pressure inside the reactor itself therefore lies between the feed-stream pressure and the effluent stream pressure.

The supported heteropolyacid may suitably be provided in the reactor in the form of one or more catalyst beds in the reactor, preferably multiple catalyst beds which may be arranged in series or in parallel. In preferred embodiments, the catalyst bed(s) is/are selected from adiabatic packed beds, tubular fixed beds or fluid beds. Most preferably the catalyst bed(s) in the reactor is/are selected from adiabatic packed beds.

Desirably, the reactor is configured such that the temperature differential across the one or more catalyst beds during drying of the supported heteropolyacid catalyst in step (i) is minimal, since this assists with uniform drying of the supported heteropolyacid catalyst. Preferably, the temperature differential across the catalyst bed(s) during drying of the supported hetereopolyacid catalyst in step (i) is no more than 20° C., preferably no more than 15° C., more preferably no more than 10° C., most preferably no more than 5° C. The temperature differential can be readily determined by means of multiple temperature sensors positioned at different locations across the catalyst bed.

The term "heteropolyacid", as used herein and throughout the description of the present invention, is deemed to include inter alia; alkali, alkali earth, ammonium, free acids, bulky cation salts, and/or metal salts (where the salts may be either full or partial salts) of heteropolyacids. Hence, the heteropolyacids used in the present invention are complex, high molecular weight anions comprising oxygen-linked polyvalent metal atoms. Typically, each anion comprises 12-18, oxygen-linked polyvalent metal atoms. The polyvalent metal atoms, known as peripheral atoms, surround one or more central atoms in a symmetrical manner. The peripheral atoms may be one or more of molybdenum, tungsten, vanadium, niobium, tantalum, or any other polyvalent metal. The central atoms are preferably silicon or phosphorus, but may alternatively comprise any one of a large variety of atoms from Groups I-VIII in the Periodic Table of elements. These include copper, beryllium, zinc, cobalt, nickel, boron, aluminium, gallium, iron, cerium, arsenic, antimony, bismuth, chromium, rhodium, silicon, germanium, tin, titanium, zirconium, vanadium, sulphur, tellurium, manganese nickel, platinum, thorium, hafnium, cerium, arsenic, vanadium, antimony ions, tellurium and iodine. Suitable heteropolyacids include Keggin, Wells-Dawson and Anderson-Evans-Perloff heteropolyacids. Specific examples of suitable heteropolyacids are as follows:

18-tungstophosphoric acid—H6[P2W18O62].xH2O
12-tungstophosphoric acid—H3[PW12O40].xH2O
12-tungstosilicic acid—H4[SiW12O40].xH2O
Cesium hydrogen tungstosilicate—Cs3H[SiW12O40].xH2O and the free acid or partial salts of the following heteropolyacids acids:

Monopotassium tungstophosphate—KH5[P2W18O62].xH2O
Monosodium 12-tungstosilicic—acid NaK3[SiW12O40].xH2O
Potassium tungstophosphate—K6[P2W18O62].xH2O
Ammonium molybdodiphosphate—(NH4)6[P2Mo18O62].xH20
Potassium molybdodivanado phosphate—K5[PMoV2O40].xH2O In addition, mixtures of different heteropolyacids and salts can be employed. The preferred heteropolyacids for use in the process described by the present invention is any one or more heteropolyacid that is based on the Keggin or Wells-Dawson structures; more preferably the chosen heteropolyacid for use in the process described by the present invention is any one or more of the following: heteropolytungstic acid (such as silicotungstic acid and phosphotungstic acid), silicomolybdic acid and phosphomolybdic acid. Most preferably, the chosen heteropolyacid for use in the process described by the present invention is any one or more silicotungstic acid, for example 12-tungstosilicic acid ($H_4[SiW_{12}O_{40}].xH_2O$).

Preferably, the heteropolyacids employed according to the present invention may have molecular weights of more than 700 and less than 8500, preferably more than 2800 and less than 6000. Such heteropolyacids also include dimeric complexes.

The supported catalyst may be conveniently prepared by dissolving the chosen heteropolyacid in a suitable solvent, where suitable solvents include polar solvents such as water, ethers, alcohols, carboxylic acids, ketones and aldehydes; distilled water and/or ethanol being the most preferable solvents. The resulting acidic solution has a heteropolyacid concentration that is preferably comprised between 10 to 80 wt %, more preferably 20 to 70 wt % and most preferably 30 to 60 wt %. This said solution is then added to the chosen support (or alternatively the support is immersed in the solution). The actual volume of acidic solution added to the support is not restricted, and hence may be enough to achieve incipient wetness or wet impregnation, where wet impregnation (i.e. preparation using an excess acidic solution volume relative to pore volume of support), is the preferred method for the purposes of the present invention.

The resulting supported heteropolyacid may be modified, and various salts of heteropolyacid may then be formed in the aqueous solution either prior to, or during, impregnation of the acidic solution onto the support, by subjecting the supported heteropolyacid to a prolonged contact with a solution of a suitable metallic salt or by addition of phosphoric acid and/or other mineral acids.

When using a soluble metallic salt to modify the support, the salt is taken in the desired concentration, with the heteropolyacid solution. The support is then left to soak in the said acidic solution for a suitable duration (e.g. a few hours), optionally with periodic agitation or circulation, after which time it is filtered, using suitable means, in order to remove any excess acid.

When the salt is insoluble it is preferred to impregnate the catalyst with the HPA and then titrate with the salt precursor. This method can improve the dispersion of the HPA salt. Other techniques such as vacuum impregnation may also be employed.

The amount of heteropolyacid impregnated on the resulting support is suitably in the range of 10 wt % to 80 wt % and preferably 20 wt % to 50 wt % based on the total weight of the heteropolyacid and the support. The weight of the catalyst on drying and the weight of the support used, may be used to obtain the weight of the acid on the support by deducting the latter from the former, giving the catalyst loading as 'g heteropolyacid/kg catalyst'. The catalyst loading in 'g heteropolyacid/liter support' can also be calculated by using the known or measured bulk density of the support. The preferred catalytic loading of heteropolyacid is 150 to 600 g heteropolyacid/kg Catalyst.

According to a preferred embodiment of the present invention the average heteropolyacid loading per surface area of the dried supported heteropolyacid catalyst is more than 0.1 micro moles/m$^2$.

It should be noted that the polyvalent oxidation states and hydration states of the heteropolyacids stated previously and as represented in the typical formulae of some specific compounds only apply to the fresh acid before it is impregnated onto the support, and especially before it is subjected to the dehydration process conditions. The degree of hydration of the heteropolyacid may affect the acidity of the supported catalyst and hence its activity and selectivity. Thus, either or both of these actions of impregnation and dehydration process may change the hydration and oxidation state of the metals in the heteropolyacids, i.e. the actual catalytic species used, under the process conditions given, may not yield the hydration/oxidation states of the metals in the heteropolyacids used to impregnate the support. Naturally therefore it is to be expected that such hydration and oxidation states may also be different in the spent catalysts after reaction According to a preferred embodiment of the present invention, the amount of chloride present in/on the said heteropolyacid supported catalyst is less than 40 ppm, preferably less than 25 ppm and most preferably less than 20 ppm.

The supported heteropolyacid catalyst used in the process of the present invention may be a fresh catalyst or a previously used catalyst. Thus, in one embodiment, at least a portion of the supported heteropolyacid catalyst has previously been employed in a process for the preparation of an ethene from a feed comprising ethanol, water and ethoxyethane. For example, at least a portion of the supported heteropolyacid may derive from an extract of heteropolyacid from a previously used catalyst i.e. from a partially deactivated material.

According to a further preferred embodiment of the present invention, the heteropolyacid supported catalyst is a heteropolytungstic acid supported catalyst having the following characteristic:

$$PV > 0.6 - 0.3 \times [\text{HPA loading/Surface Area of Catalyst}]$$

wherein PV is the pore volume of the dried supported heteropolytungstic acid catalyst (measured in ml/g catalyst); HPA loading is the amount of heteropolyacid present in the dried supported heteropolyacid catalyst (measured in micro moles per gram of catalyst) and Surface Area of Catalyst is the surface area of the dried supported heteropolytungstic acid catalyst (measured in m$^2$ per gram of catalyst).

Suitable catalyst supports may be in a powder form or alternatively may be in a granular form, or in a pelletised form, a spherical form or as extrudates (including shaped particles) and include, but are not limited to, clays, bentonite, diatomous earth, titania, activated carbon, aluminosilicates e.g. montmorillonite, alumina, silica-alumina, silica-titania cogels, silica-zirconia cogels, carbon coated alumina, zeolites, zinc oxide, flame pyrolysed oxides. Supports can be mixed oxides, neutral or weakly basic oxides. Silica supports are preferred, such as silica gel supports and supports produced by the flame hydrolysis of SiCl$_4$. Preferred supports are substantially free of extraneous metals or elements which might adversely affect the catalytic activity of the system. Thus, suitable silica supports are typically at least 99% w/w pure. Impurities amount to less than 1% w/w, preferably less than 0.60% w/w and most preferably less than 0.30% w/w. The pore volume of the support is preferably more than 0.50 ml/g and preferably more than 0.8 ml/g.

Suitable silica supports include, but are not limited to any of the following: Grace Davison Davicat® Grade 57, Grace Davison Davicat® 1252, Grace Davison Davicat® SI 1254, Fuji Silysia CariAct® Q15, Fuji Silysia CariAct® Q10, Degussa Aerolyst® 3045 and Degussa Aerolyst® 3043.

The average diameter of the supported heteropolyacid particles is preferably from 500 µm to 8,000 µm; more preferably from 1,000 µm to 7,000 µm; even more preferably from 2,000 µm to 6,000 µm, most preferably from 3,000 µm to 5,000 µm. It has been surprisingly found that the effects of the present invention are enhanced with supported heteropolyacid particles of larger size (i.e. falling within the above ranges). However, in some embodiments, these particles may be crushed and sieved to smaller sizes of, for example, 50-2,000 µm, if desired.

The average pore radius (prior to impregnation with the heteropolyacid) of the support is 10 to 500 Å, preferably 30 to 350 Å, more preferably 50 to 300 Å and most preferably 60 to 250 Å. The BET surface area is preferably between 50 and 600 m$^2$/g and is most preferably between 130 and 400 m$^2$/g.

The BET surface area, pore volume, pore size distribution and average pore radius were determined from the nitrogen adsorption isotherm determined at 77K using a Micromeritics TRISTAR 3000 static volumetric adsorption analyser. The procedure used was an application of British Standard methods BS4359: Part 1: 1984 'Recommendations for gas adsorption (BET) methods' and BS7591: Part 2: 1992, 'Porosity and pore size distribution of materials'—Method of evaluation by gas adsorption. The resulting data were reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am Chem. Soc., 1951 73 373-380.

Samples of the supports and catalysts were out gassed for 16 hours at 120° C. under a vacuum of $5\times10^{-3}$ Torr (0.6666 Pa) prior to analysis.

In another aspect, the present invention also provides a use of a dried supported heteropolyacid catalyst prepared by the initiation procedure described hereinbefore for improving ethene productivity and/or for extending catalyst lifetime in a process for producing ethene by the vapour phase chemical dehydration of a feed-stream comprising ethanol and optionally water and/or ethoxyethane, wherein said process comprises contacting a supported heteropolyacid catalyst with the feed-stream having a feed temperature of at least 200° C.

In other aspects, the present invention also provides a composition comprising (or consisting of) a product obtained by a process according to the present invention and/or derivatives thereof, including a product obtained by a process according to the present invention per se, and/or derivatives thereof. As used herein, a derivative is a composition comprising or consisting of a product arising from a further process, said further process having utilised the product of the present invention as a feedstock at any stage. By way of non-limiting example, polyethylene may be such a derivative. As the composition/product described here arises from a process as described above, any features of the process described above are also applicable to these aspects, either individually or in any combination.

The present invention will now be illustrated by way of the following examples and with reference to the following figures:

FIG. 1: Graphical representation of ethene productivity against time of catalyst exposure to a feed stream at 260° C. for Example 1 and Comparative Examples 1 to 3; and FIG. 2: Graphical representation of ethene productivity against time of catalyst exposure to a feed stream at 260° C. for Example 2 and Comparative Example 4.

CATALYST PREPARATION

A silicotungstic acid (STA) catalyst was used for conducting the dehydration reactions according to the following examples.

A high purity silica support with a surface area of 147 m²/g, pore volume of 0.84 ml/g and a mean pore diameter of 230 Å was used for preparation of the STA catalyst. The catalyst was prepared by adding silica (512 g) to a solution of silicotungstic acid (508 g) in water (1249 g). Once the silicotungstic acid solution had fully impregnated the pores of the support the excess solution was drained, under gravity, from the support and this was then dried.

The STA loading on the catalyst support as STA.$6H_2O$, on a dry weight basis, was estimated to be 24.5% w/w, based on the weight gained by the silica during the catalyst preparation.

For Example 1 and Comparative Examples 1 to 3 below, the catalyst was crushed to a particle size of 100 to 200 μm before being loaded into the reactor tube.

For Example 2 and Comparative Example 4 below, the catalyst was crushed to a particle size of 850 to 1000 μm before being loaded into the reactor tube.

Vapour Phase Dehydration Reactions for Example 1 and Comparative Examples 1 to 3

A mass of STA catalyst (as indicated in Table 1 below) prepared in accordance with the above method was loaded into a reactor tube having an isothermal bed and pressurised to 0.501 MPa under inert gas (nitrogen and helium) flow. The catalyst was heated at 2° C./min to either 150° C. (Example 1) or 240° C. (Comparative Examples 1 to 3) under a combined nitrogen (0.01500 mol/hr) and helium flow (0.00107 mol/hr) and held at this temperature for 8 hours before being cooled to 150° C., if not already at this temperature.

Ethanol (0.04084 mol/hr) was then added to the nitrogen/helium flow and the temperature was increased at 2° C./min to 225° C. Once at 225° C. the feed pressure was increased at a rate of 0.1 MPa/min such that the pressure inside the reactor was increased to the value of 2.858 MPa. The diethyl ether and water reagents were added to the ethanol, helium and nitrogen flow. At this point the flows of the feed components were adjusted to give ethanol (0.02677 mol/hr), diethyl ether (0.00776 mol/hr), water (0.00297 mol/hr), helium (0.00106 mol/hr) and nitrogen (0.01479 mol/hr).

Once the catalyst performance had stabilised at 225° C., typically after around 100 hrs, the catalyst temperature, which is the same as the feed temperature in this particular reactor, was increased to 260° C. and the ethene productivity monitored versus time by on-line GC analysis. The results of dehydration experiments at varying pressure are presented in Table 1 below.

TABLE 1

| Example | Max. Temp. under $N_2$ flow (° C.) | Mass of catalyst (mg) | Time on Stream at 260° C. (hrs) | Process Temp. (° C.) | Total Pressure (MPa) | Ethylene Productivity (mole/kg catalyst/hr) |
|---|---|---|---|---|---|---|
| Example 1 | 150 | 27.2 | 4.11 | 260 | 2.858 | 478 |
| Example 1 | 150 | 27.2 | 37.8 | 260 | 2.858 | 397 |
| Example 1 | 150 | 27.2 | 72.47 | 260 | 2.858 | 379 |
| Example 1 | 150 | 27.2 | 139.84 | 260 | 2.858 | 281 |
| Example 1 | 150 | 27.2 | 186.99 | 260 | 2.858 | 268 |
| Example 1 | 150 | 27.2 | 207.19 | 260 | 2.858 | 263 |
| Example 1 | 150 | 27.2 | 254.33 | 260 | 2.858 | 215 |
| Comparative Example 1 | 240 | 27.16 | 0.84 | 260 | 2.858 | 411 |
| Comparative Example 1 | 240 | 27.16 | 27.97 | 260 | 2.858 | 314 |
| Comparative Example 1 | 240 | 27.16 | 48.14 | 260 | 2.858 | 271 |
| Comparative Example 1 | 240 | 27.16 | 81.94 | 260 | 2.858 | 239 |
| Comparative Example 1 | 240 | 27.16 | 115.66 | 260 | 2.858 | 164 |
| Comparative Example 1 | 240 | 27.16 | 183.1 | 260 | 2.858 | 9 |
| Comparative Example 1 | 240 | 27.16 | 230.26 | 260 | 2.858 | 5 |

TABLE 1-continued

| Example | Max. Temp. under N$_2$ flow (° C.) | Mass of catalyst (mg) | Time on Stream at 260° C. (hrs) | Process Temp. (° C.) | Total Pressure (MPa) | Ethylene Productivity (mole/kg catalyst/hr) |
|---|---|---|---|---|---|---|
| Comparative Example 1 | 240 | 27.16 | 250.43 | 260 | 2.858 | 5 |
| Comparative Example 2 | 240 | 27.3 | 5.36 | 260 | 2.858 | 397 |
| Comparative Example 2 | 240 | 27.3 | 38.97 | 260 | 2.858 | 344 |
| Comparative Example 2 | 240 | 27.3 | 72.67 | 260 | 2.858 | 257 |
| Comparative Example 2 | 240 | 27.3 | 139.89 | 260 | 2.858 | 210 |
| Comparative Example 2 | 240 | 27.3 | 186.95 | 260 | 2.858 | 101 |
| Comparative Example 3 | 240 | 27.1 | 5.77 | 260 | 2.858 | 342 |
| Comparative Example 3 | 240 | 27.1 | 32.67 | 260 | 2.858 | 287 |
| Comparative Example 3 | 240 | 27.1 | 66.29 | 260 | 2.858 | 232 |
| Comparative Example 3 | 240 | 27.1 | 140.99 | 260 | 2.858 | 154 |
| Comparative Example 3 | 240 | 27.1 | 200.38 | 260 | 2.858 | 30 |
| Comparative Example 3 | 240 | 27.1 | 257.72 | 260 | 2.858 | 4 |

The results in Table 1, which are represented graphically in FIG. 1, illustrate the benefits of the process of the invention with regard to catalyst lifetime. It is clear from FIG. 1 that ethene productivity remains high with Example 1, which benefits from having had a catalyst drying step at a temperature of 150° C. in accordance with the invention, for a significantly longer period of time compared with Comparative Examples 1 to 3, which have had a catalyst drying step at high temperature (240° C.) not in accordance with the present invention. FIG. 1 also illustrates that the maximum ethene productivity in the ethanol dehydration reaction may also be increased by virtue of a drying step according to the present invention, in comparison with a high temperature drying step not in accordance with the invention as in the case of Comparative Examples 1 to 3. The maximum ethene productivity observed for Example 1 was 478 mole/kg catalyst/hr, whilst the maximum ethene productivity observed for Comparative Examples 1 to 3 was only 411 mole/kg catalyst/hr (Comparative Example 1).

Vapour Phase Dehydration Reactions for Example 2 and Comparative Example 4

A mass of STA catalyst (as indicated in Table 2 below) prepared in accordance with the above method described above was loaded into a reactor tube and pressurised to 0.5 MPa under nitrogen flow. The catalyst was heated to either 150° C. or 240° C. under nitrogen (0.4957 mol/hr) flow and held at this temperature for 2 hours before being cooled to 150° C., if not already at this temperature.

Ethanol (1.3228 mol/hr) was then added to the nitrogen flow and the temperature of the feed to the catalyst bed was increased to 225° C. Once at 225° C. the feed pressure was increased to the value of 2.857 MPa. The diethyl ether and water reagents were then added to the ethanol and nitrogen flow. At this point the flows of the feed components were adjusted to give ethanol (0.8544 mol/hr), diethyl ether (0.2476 mol/hr), water (0.0949 mol/hr) and nitrogen (0.4957 mol/hr).

After 24 hrs the temperature of the feed to the catalyst bed was increased to 260° C. and the ethylene productivity monitored versus time by on-line GC analysis. The results of dehydration experiments at varying pressure are presented in Table 2 below.

TABLE 2

| Example | Max. Temp. under N$_2$ flow (° C.) | Mass of catalyst (g) | Time on Stream at 260° C. (hrs) | Process Temp. (° C.) | Total Pressure (MPa) | Ethylene Productivity (mole/kg catalyst/hr) |
|---|---|---|---|---|---|---|
| Example 2 | 150 | 0.507 | 0 | 260 | 2.857 | 444 |
| Example 2 | 150 | 0.507 | 15 | 260 | 2.857 | 427 |
| Example 2 | 150 | 0.507 | 29 | 260 | 2.857 | 424 |
| Example 2 | 150 | 0.507 | 45 | 260 | 2.857 | 413 |
| Example 2 | 150 | 0.507 | 59 | 260 | 2.857 | 415 |
| Example 2 | 150 | 0.507 | 89 | 260 | 2.857 | 402 |
| Example 2 | 150 | 0.507 | 115 | 260 | 2.857 | 411 |
| Example 2 | 150 | 0.507 | 130 | 260 | 2.857 | 415 |
| Example 2 | 150 | 0.507 | 145 | 260 | 2.857 | 410 |
| Example 2 | 150 | 0.507 | 160 | 260 | 2.857 | 395 |
| Example 2 | 150 | 0.507 | 175 | 260 | 2.857 | 410 |
| Example 2 | 150 | 0.507 | 190 | 260 | 2.857 | 404 |
| Example 2 | 150 | 0.507 | 206 | 260 | 2.857 | 401 |
| Comparative Example 4 | 240 | 0.508 | 0 | 260 | 2.857 | 436 |
| Comparative Example 4 | 240 | 0.508 | 16 | 260 | 2.857 | 402 |
| Comparative Example 4 | 240 | 0.508 | 30 | 260 | 2.857 | 398 |
| Comparative Example 4 | 240 | 0.508 | 45 | 260 | 2.857 | 383 |
| Comparative Example 4 | 240 | 0.508 | 60 | 260 | 2.857 | 376 |
| Comparative Example 4 | 240 | 0.508 | 115 | 260 | 2.857 | 335 |
| Comparative Example 4 | 240 | 0.508 | 130 | 260 | 2.857 | 334 |
| Comparative Example 4 | 240 | 0.508 | 145 | 260 | 2.857 | 330 |
| Comparative Example 4 | 240 | 0.508 | 160 | 260 | 2.857 | 319 |
| Comparative Example 4 | 240 | 0.508 | 176 | 260 | 2.857 | 316 |
| Comparative Example 4 | 240 | 0.508 | 191 | 260 | 2.857 | 300 |
| Comparative Example 4 | 240 | 0.508 | 206 | 260 | 2.857 | 287 |

Figure 2:
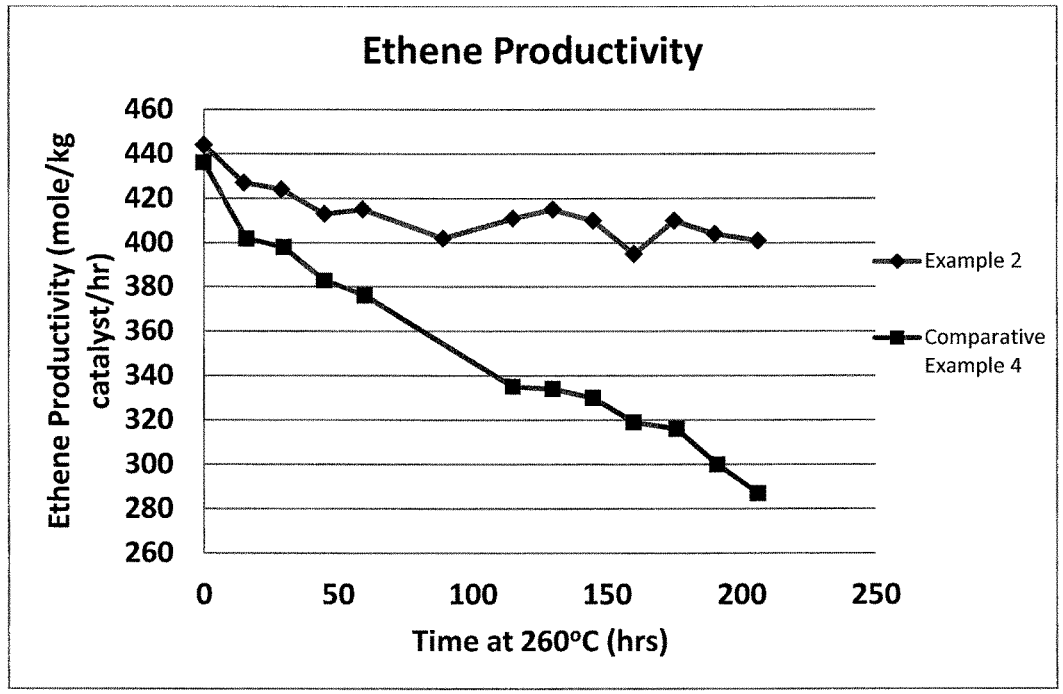

The results in Table 2, which are represented graphically in FIG. 2, illustrate the benefits of the process of the invention with regard to catalyst lifetime. It is clear from FIG. 2 that ethene productivity remains high with Example 2, which benefits from having had a catalyst drying step at a temperature of 150° C. in accordance with the invention, for a significantly longer period of time compared with Comparative Example 4, which has had a catalyst drying step at high temperature (240° C.) not in accordance with the present invention. It will also be appreciated that ethene productivity is generally higher for Example 2 than for Example 1. For instance, even after 206 hours on stream, the ethene productivity for Example 2 is above 401 mole/kg catalyst/hr, whereas after 207 hours on stream the ethene productivity for Example 2 is above 263 mole/kg catalyst/hr.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A process for the preparation of ethene by vapour phase chemical dehydration of a feed-stream comprising ethanol and optionally water and/or ethoxyethane, said process comprising contacting a dried supported heteropolyacid catalyst in a reactor with the feed-stream having a feed temperature of at least 200° C.; wherein before the supported heteropolyacid catalyst is contacted with the feed-stream having a feed temperature of at least 200° C., the process is initiated by:
(i) drying a supported heteropolyacid catalyst in a reactor under a stream of inert gas having a feed temperature of from above 100° C. to 200° C. to form a dried supported heteropolyacid catalyst; and
(ii) contacting the dried supported heteropolyacid catalyst with an ethanol-containing vapour stream having a feed temperature of from above 100° C. to 160° C.

2. The process according to claim 1, wherein the supported heteropolyacid catalyst is dried in step (i) under a stream of inert gas having a feed temperature of from 100° C. to 180° C.

3. The process according to claim 1, wherein the dried supported heteropolyacid catalyst is contacted in step (ii) with an ethanol-containing vapour stream having a feed temperature of from 120° C. to 158° C.

4. The process according to claim 1, wherein the feed temperature of the feed-stream is at least 220° C.

5. The process according to claim 1, wherein the upper limit of the feed temperature of the feed-stream is 350° C.

6. The process according to claim 1, wherein the pressure inside the reactor when the supported heteropolyacid catalyst is contacted with the feed-stream is from 0.1 MPa to 4.5 MPa.

7. A process according to claim 1, wherein the initiation of the ethanol dehydration process further comprises: (iii) ramping the feed temperature of the ethanol-containing vapour stream to at least 200° C.

8. The process according to claim 1, wherein the feed-stream comprises water and/or ethoxyethane.

9. The process according to claim 1, wherein the ethanol-containing vapour stream comprises or consists of ethanol, any balance being made up of inert gas diluents.

10. The process according to claim 1, wherein drying in step (i) is undertaken for a period of from 1 to 48 hours.

11. The process according to claim 1, wherein the catalyst is provided in the form of one or more catalyst beds in the reactor.

12. The process according to claim 11, wherein the catalyst is provided in the form of multiple catalyst beds arranged in series or in parallel.

13. The process according to claim 11, wherein the catalyst bed(s) is/are selected from adiabatic packed beds, tubular fixed beds or fluid beds.

14. The process according to claim 11, wherein the temperature differential across the bed of supported hetereopolyacid catalyst in the reactor during drying of the supported hetereopolyacid catalyst in step (i) is no more than 20° C.

15. The process according to claim 1, wherein the average diameter of the supported heteropolyacid catalyst particles is from 500 μm to 8,000 μm.

16. The process according to claim 1, wherein the amount of heteropolyacid in the supported heteropolyacid catalyst is in the range of from 10 wt. % to 50 wt. % based on the total weight of the supported heteropolyacid catalyst.

17. The process according to claim 1, wherein at least a portion of the supported heteropolyacid catalyst has previously been employed in a process for the preparation of an ethene from a feed-stream comprising ethanol, water and ethoxyethane.

18. The process according to claim 1, wherein the supported heteropolyacid catalyst is a supported heteropolytungstic acid catalyst.

19. The process according to claim 1, wherein the feed temperature of the feed-stream is at least 220° C. and the upper limit of the feed temperature of the feed-stream is 325° C.

20. A process according to claim 1, wherein the pressure inside the reactor is from 1.0 MPa to 2.8 MPa.

* * * * *